United States Patent
Pastl

(10) Patent No.: US 12,239,537 B2
(45) Date of Patent: Mar. 4, 2025

(54) BONE TRANSPLANT

(71) Applicant: SURGEBRIGHT GMBH, Lichtenberg (AT)

(72) Inventor: Klaus Pastl, Lichtenberg (AT)

(73) Assignee: SURGEBRIGHT GMBH, Lichtenberg (AT)

(*) Notice: Subject to any disclaimer, the term of this patent is extended or adjusted under 35 U.S.C. 154(b) by 116 days.

(21) Appl. No.: 17/423,342

(22) PCT Filed: Dec. 10, 2019

(86) PCT No.: PCT/EP2019/084519
§ 371 (c)(1),
(2) Date: Jul. 15, 2021

(87) PCT Pub. No.: WO2020/148025
PCT Pub. Date: Jul. 23, 2020

(65) Prior Publication Data
US 2022/0096239 A1 Mar. 31, 2022

(30) Foreign Application Priority Data
Jan. 16, 2019 (AT) .............................. A 50034/2019

(51) Int. Cl.
*A61B 17/86* (2006.01)
*A61B 17/56* (2006.01)
(Continued)

(52) U.S. Cl.
CPC ........ *A61F 2/28* (2013.01); *A61F 2002/2839* (2013.01); *A61F 2002/3021* (2013.01);
(Continued)

(58) Field of Classification Search
None
See application file for complete search history.

(56) References Cited

U.S. PATENT DOCUMENTS 6,045,554 A * 4/2000 Grooms ............. A61B 17/8891
606/76
6,048,204 A * 4/2000 Klardie ................ A61C 8/0022
433/174
(Continued)

FOREIGN PATENT DOCUMENTS

| AT | 522112 B1 | 1/2021 |
| EP | 2 384 712 B1 | 3/2014 |
| WO | 2019/034522 | 2/2019 |

OTHER PUBLICATIONS

International Search Report issued in International Patent Application No. PCT/EP2019/084519, dated Mar. 2, 2020, along with an English translation thereof.
(Continued)

*Primary Examiner* — Ann Hu
(74) *Attorney, Agent, or Firm* — GREENBLUM & BERNSTEIN, P.L.C.

(57) ABSTRACT

Bone transplant made of a cortical bone substance having a screw shank and a screw head for introducing a screwing-in torque. Both the screw shank and the screw head are provided with an external thread, in which at least the external thread of the screw shank is a multi-start thread. Due to the design, on the one hand a certain stroke can be achieved with fewer revolutions or in a shorter time, whereby the screwing-in behavior is improved and the tendon tissue is protected. On the other hand, the use of multiple threads provides a high surface area for the tendon tissue to grow on the tendon anchor, which improves fixation of the tendon and increases rotational stability. The bone transplant according to the invention thus ensures good fixation of the tendon and can be implanted quickly.

5 Claims, 1 Drawing Sheet

(51) Int. Cl.
*A61B 17/88* (2006.01)
*A61F 2/28* (2006.01)
*A61F 2/30* (2006.01)

(52) U.S. Cl.
CPC ............... *A61F 2002/30224* (2013.01); *A61F 2002/30851* (2013.01); *A61F 2310/00359* (2013.01)

(56) References Cited

U.S. PATENT DOCUMENTS

| | | | | |
|---|---|---|---|---|
| 8,197,523 | B2* | 6/2012 | Bottlang | A61B 17/863 |
| | | | | 606/301 |
| 8,702,768 | B2* | 4/2014 | Tipirneni | A61B 17/742 |
| | | | | 606/320 |
| 10,918,430 | B2* | 2/2021 | Bottlang | A61B 17/8042 |
| 11,224,467 | B2* | 1/2022 | Peterson | A61B 17/869 |
| 11,744,624 | B2* | 9/2023 | Pastl | A61B 17/866 |
| | | | | 606/305 |
| 2002/0038123 | A1* | 3/2002 | Visotsky | A61B 17/8095 |
| | | | | 606/907 |
| 2002/0052605 | A1 | 5/2002 | Grooms et al. | |
| 2003/0135214 | A1 | 7/2003 | Fetto et al. | |
| 2005/0038438 | A1* | 2/2005 | Anderson | A61B 17/7071 |
| | | | | 606/328 |
| 2006/0100626 | A1* | 5/2006 | Rathbun | A61B 17/1728 |
| | | | | 606/280 |
| 2006/0110707 | A1* | 5/2006 | Perez Davidi | A61C 8/0024 |
| | | | | 433/173 |
| 2008/0188899 | A1* | 8/2008 | Bottlang | A61B 17/8057 |
| | | | | 606/301 |
| 2009/0082814 | A1* | 3/2009 | Bickley | A61B 17/686 |
| | | | | 606/301 |
| 2010/0240010 | A1* | 9/2010 | Holmstrom | A61C 8/0025 |
| | | | | 433/173 |
| 2012/0029579 | A1* | 2/2012 | Bottlang | A61B 17/80 |
| | | | | 606/315 |
| 2013/0273499 | A1* | 10/2013 | Hansson | A61C 8/0022 |
| | | | | 433/173 |
| 2017/0231674 | A1 | 8/2017 | Weiss et al. | |
| 2018/0028236 | A1 | 2/2018 | Ziemek et al. | |

OTHER PUBLICATIONS

Written Opinion of the International Searching Authority issued in International Patent Application No. PCT/EP2019/084519, dated Mar. 2, 2020, along with an English translation thereof.

* cited by examiner

BONE TRANSPLANT

BACKGROUND

1. Field of the Invention

The invention relates to a bone transplant of a cortical bone substance having a screw shank and a screw head for introducing a screwing-in torque, wherein both the screw shank and the screw head are provided with an external thread, according to the preamble of claim 1.

2. Description of the Background

Screws for surgical procedures are conventionally made of metal or metal alloys. Screws made of resorbable material, such as polyglycolide and polylactide, are also known. However, screws of this type have several disadvantages in surgical practice. For example, screws made of metal or metal alloys must be removed by a second operation and are subject to changes due to corrosion. This increases the costs for the health care system as well as the health risks for each patient due to a new operation. All resorbable materials are dissolved, but during their degradation they can lead to large osteolyses in the surrounding bone, i.e. the recipient bone moves away from the screw. Osteolytic processes can lead to loosening and eventual breakout of the implant. Bioresorption, in turn, is a year-long process that may be accompanied by inflammation and pain.

Screws made of allogeneic bone (femur and tibia corticalis), such as those known from the applicant's PCT/EP2018/071619, which is considered to be the closest prior art for the present invention, on the other hand, have several advantages. They are vascularized and remodeled without rejection, and are suitable for osteosyntheses, for example, where small bone fragments have to be joined together, since the screw already creates a load-bearing bone bridge during surgery, which improves from the time of surgery by remodeling and becoming fully integrated and incorporated into the living bone. Screws with a diameter of 3-4 mm, for example, will become fully vascularized within two months. These bone screws can therefore be called bone transplants. In contrast, metal screws are more of an obstacle to new bone formation; in particular, their mere presence reduces the available surface area that would be available for bone healing. Degradable materials, on the other hand, have their maximum strength at the time of surgery. The same disadvantages apply to them as to the metal screws. Furthermore, the strength decreases rapidly as soon as the degradation process occurs, causing the bone site to be osteosynthesized to weaken again, at least temporarily.

These disadvantages are particularly evident in the manufacture of tendon anchors. Tendon anchors are used to refix tendons to bones. A screw conventionally made of metal is screwed into a prefabricated hole with the aid of a screwing tool, wherein the end of the tendon is fixed by frictional engagement between the prefabricated hole and the inserted screw. The use of a tendon anchor made of a metallic material or a plastic reduces the surface area available for tendon attachment and causes disturbing artifacts in subsequent imaging procedures such as MRI and CT.

When using bone transplants from allogeneic bone, these disadvantages could be avoided, since the surface of the bone transplant also allows the tendon to grow and thus significantly increases the surface available for the tendon to grow. However, when using screws made from allogeneic bone in surgical practice, it must be noted that they differ significantly from metal screws in terms of insertion resistance and strength. Since they are derived from allogeneic human cortical bone, it is not expected that knowledge of thread form, screwing-in resistance, rotational stability or strength as known from metal screws can be transferred without further ado.

A further challenge in the use of bone transplants as tendon anchors lies in the loads exerted by the tendon on the bone transplant. Despite the loads, the bone transplant must ensure a secure hold of the tendon and exhibit a high degree of rotational stability, i.e. a high degree of self-locking against unwanted rotation and thus loosening of the screw. By using as small a thread pitch as possible, and thus as many turns of the same thread as possible per axial unit of length, the surface area for growing the tendon could be increased, resulting in better hold of the tendon. In addition, rotational stability can be increased in this way. On the other hand, the smaller the thread pitch, the greater the stress on the tendon tissue when the bone transplant is screwed in, since in this case the connective tissue fibers of the tendon tend to be unraveled and the tendon loses strength in its attachment points to the bone. Instead, it would be advantageous to apply as little stress as possible to the tendon parts located between the tendon anchor and the surrounding bone during screw insertion to avoid damage to the tendon tissue. In addition, the lower the thread pitch of the screw, the higher the number of turns required to insert the screw. This sometimes proves to be problematic in surgical practice, especially for sites that are difficult to access. This situation is also referred to below as screwing-in behavior, wherein good screwing-in behavior is characterized by rapid and easy insertion of the screw.

SUMMARY

It is therefore the object of the invention to optimize bone transplants from cortical bone for use as tendon anchors. In particular, they should ensure good fixation of the tendon and be quickly implantable.

These objects are achieved by the features of claim 1. Claim 1 relates to a bone transplant of a cortical bone substance having a screw shank and a screw head for introducing a screwing-in torque, wherein both the screw shank and the screw head are provided with an external thread. According to the invention, it is proposed here that at least the external thread of the screw shank is a multi-start thread.

In multi-start threads, at least two threads are "wrapped" parallel around the screw shank. In this way, the pitch of each thread turn and thus the thread stroke of the screw can be increased. The intermediate space not required by one thread turn is filled by a second thread turn or further thread turns. In this way, on the one hand, a certain stroke can be achieved with fewer turns or in a shorter time, which improves the screwing-in behavior and protects the tendon tissue. On the other hand, the use of multiple threads provides a high surface area for the tendon tissue to grow on the tendon anchor, which improves fixation of the tendon and increases rotational stability. The bone transplant according to the invention thus ensures good fixation of the tendon and can be implanted quickly.

According to one possible embodiment, for example, it is proposed that the multi-start thread comprises two threads, each of which has a pitch of between 0.8 mm and 3 mm. For this purpose, the bone transplant according to the invention is designed in the shape of a cone in terms of its dimensions and thus has a cylindrical section proximally which merges distally into a conical section. The ratio of thread depth t to thread outer diameter D is preferably between 0.10 and 0.25.

Preferably, the thread is a pointed thread. The pointed thread not only optimizes the surface available for the growth of the tendon tissue on the tendon anchor, but also offers practical advantages in the manufacture of the bone transplant according to the invention, since the pointed thread can be arranged along the circumference of the screw with less space requirement.

According to the invention, the screw head is also provided with an external thread and thus contributes to the strength of the tendon attachment. In particular, the screw head can also be screwed into the bone without having to be cut off. For the introduction of a screwing-in torque, it is preferably proposed that at least two recesses for receiving a screwing-in tool are provided, which recesses are distributed around the screw head axis, extend axially in the direction of the screw head axis and open into the end face of the free end of the screw head, wherein the recesses are each formed by lateral surfaces which extend in the direction of the screw head axis from an outer lateral surface enveloping the external thread of the screw head and merge into one another in a surface section near the axis. The external thread of the screw head is thus interrupted only by the axially extending recesses provided for introducing a screwing-in torque. The bone transplant is otherwise drill-free and consists entirely of bone material. In the area of the screw head axis in particular, bone material thus remains; only axial recesses are milled into the outer shell of the screw head, which open into the proximal end face of the screw head. Axial extensions of an insertion tool can be inserted axially into these recesses on the face side. The screwing-in torque is then exerted on the side surfaces of the recesses, wherein the screwing-in torque is applied in a kinematically favorable manner in the outer circumferential region of the screw head.

To increase the screwing-in torque, it is also proposed to provide four recesses distributed symmetrically around the screw head axis. In the case of four recesses arranged symmetrically around the screw head axis, the screw head areas remaining between the recesses are gripped and "clamped" to a certain extent by the extensions of the insertion tool during the axial insertion of the extensions of the insertion tool in the case of diameters in the single-digit millimeter range customary for bone screws, thus preventing bone material from breaking off. The proposed recesses also allow the outer diameter of the screw head to be aligned with the outer diameter of the screw shank and with the outer diameter of the screwing-in tool, thus enabling new surgical applications such as endoscopic or arthroscopic use of the screw.

The bone transplant can be of cylindrical or frustoconical design. The threaded outer diameter of the bone transplant is preferably between 7.0 mm and 4.5 mm. The length of the bone transplant is at least three times the diameter of the bone transplant in the case of a cylindrical design and at least three times the largest diameter of the bone transplant in the case of a frustoconical design of the bone transplant.

BRIEF DESCRIPTION OF THE DRAWING

The invention is explained in more detail below by means of exemplary embodiments with the aid of the accompanying figures, wherein:

FIG. 2 shows an embodiment of a bone transplant according to the invention, wherein

DETAILED DESCRIPTION

Figure 1:
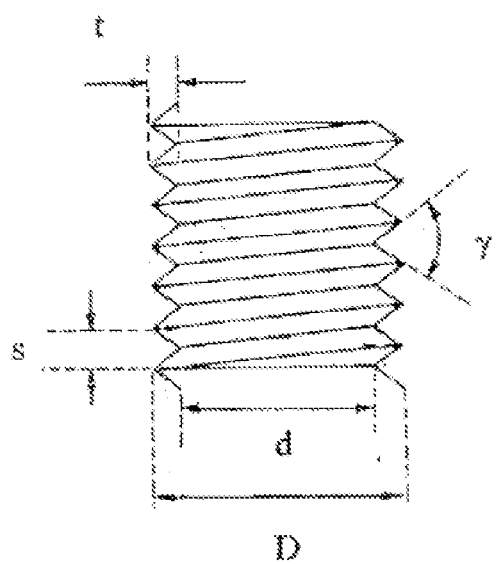
FIG. 1 shows a thread section of a pointed thread to explain the relevant thread parameters.

FIG. 1 is used to explain the relevant thread parameters. These are the thread outside diameter D and the core diameter d, wherein the thread depth t is determined by their difference, and the pitch s of the thread, wherein the pitch s is the distance covered by one revolution of the screw, i.e. the distance between two thread tips of the same thread, which is given in millimeters for metric threads. The reciprocal of the pitch s usually corresponds to the number of turns of a thread per unit length, i.e. the number of turns per millimeter for metric threads. Another parameter is the flank angle γ, which in turn results from the thread depth t and the pitch s.

The larger the flank angle γ at constant thread depth t, the fewer turns per mm are available for the tendon attachment. As a result, the strength of the tendon attachment and the rotational stability of the screw decrease. On the other hand, the thread stroke is increased, so that the screwing-in behavior is promoted for surgical practice. On the other hand, the smaller the thread pitch, the greater the stress on the tendon tissue when the bone transplant is screwed in. With the aid of the features according to the invention, these contradictory requirements can be resolved to optimize the tendon anchor.

For this purpose, reference is made to FIG. 2, which shows an embodiment of a bone transplant made of a cortical bone substance for surgical use as a tendon anchor. The bone transplant has a cylindrical screw shank 1, which is provided with an external thread, and a screw head 2 for introducing a screwing-in torque, which also heals in and does not have to be cut away like conventional screw heads. The screw head 2 is also provided with an external thread and has an outer lateral surface enveloping the external thread of the screw head, which is rotationally symmetrical about the screw head axis S. The screw head 2 further has four recesses 3, which are distributed around the screw head axis S, extend axially in the direction of the screw head axis S and open into the end face of the free end of the screw head 2, for receiving a screwing-in tool. The axially extending recesses 3 are each formed by side surfaces 4 extending from the outer lateral surface in the direction of the screw head axis S, which merge into one another in a surface section close to the axis (see in particular FIG. 2a). The side surfaces 4 of the recesses 3 extending from the outer lateral surface in the direction of the screw head axis S can be convex, and the surface section near the axis can be concave.

Figure 2A:
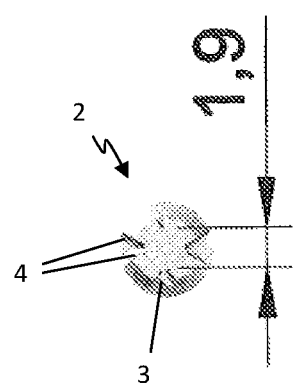
FIG. 2a shows the bone transplant according to the invention viewed from above so that the screw head is visible.
Figure 2B:
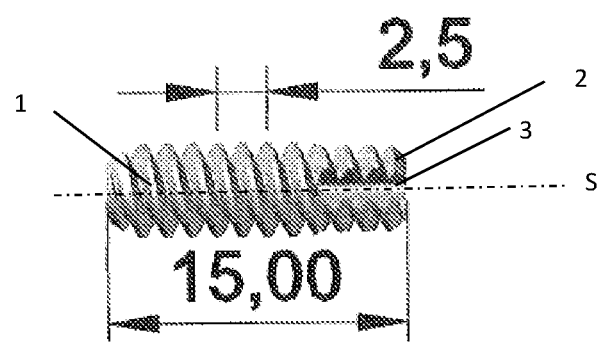
FIGS. 2b and 2c show the bone transplant according to the invention as seen from the side.
Figure 2C:
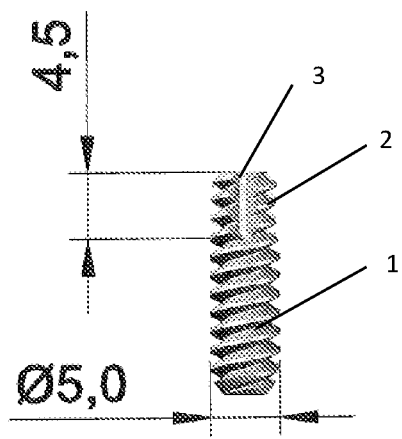
Figure 2D:
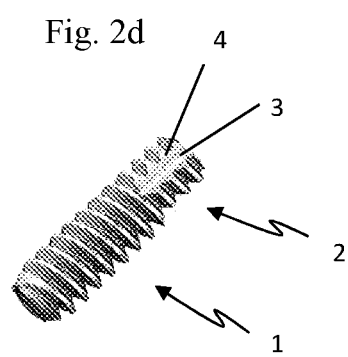
FIG. 2d shows a perspective view of a bone transplant according to the invention.

As can be seen from FIGS. 2a-2d, in the embodiment shown with unchanged thread parameters, the external thread extends over both the screw shank 1 and the screw head 2. The screw head 2 thus contributes to the strength of the tendon attachment. In particular, the screw head 2 can also be screwed into the bone without having to be cut off. The external thread is interrupted only by the axially extending recesses 3 provided for introducing a screwing-in torque. Bone material with a core diameter d thus remains in the area of the screw head axis S, as can be seen in FIG. 2a, since only axial recesses 3 are milled into the outer shell of the screw head 2, which open into the proximal end face of the screw head 2. Axial extensions of a screwing-in tool can be inserted axially into these recesses 3 at the end face. The screwing-in torque is then exerted on the side surfaces 4 of the recesses 3.

According to the invention, the external thread is designed as a multi-start thread. According to the embodiment of FIG. 2, the external thread of the screw shank 1 and of the screw head 2 is approximately designed as a multi-start thread with two thread turns, each having a pitch of 2.5 mm. The total length of the screw shown is 15 mm with a thread outer diameter D of 5 mm. The axial length of the recesses 3 of the screw head 2 is 4.5 mm, with the remaining core diameter d of the screw head being 1.9 mm.

By using a multi-start thread, the pitch s of each thread and thus the thread stroke of the screw can be increased. In this way, on the one hand, a certain stroke can be achieved with fewer revolutions or in a shorter time, which improves the screwing-in behavior and protects the tendon tissue. On the other hand, the use of multiple threads provides a high surface area for the tendon tissue to grow on the tendon anchor, which improves fixation of the tendon and increases rotational stability. The bone transplant according to the invention thus ensures good fixation of the tendon and can be implanted quickly.

The invention claimed is:

1. A bone transplant made of a cortical bone substance, said bone transplant comprising:
   a screw shank being cylindrical; and
   a screw head configured to introduce a screwing-in torque;
   axial recesses milled into an outer shell of the screw head, which open into a proximal end face of the screw head;
   both the screw shank and the screw head are provided with an external thread;
   the bone transplant is a tendon anchor for refixation of tendons to bones;
   at least the external thread of the screw shank is a multi-start thread; and
   the bone transplant is drill free and has a length at least three times a diameter of the bone transplant.

2. The bone transplant according to claim 1, wherein:
   the multi-start thread comprises two threads each having a pitch between 0.8 mm and 3 mm.

3. The bone transplant according to claim 1, wherein:
   the thread is a pointed thread.

4. The bone transplant according to claim 1, wherein:
   the axial recesses are configured to receive a screwing-in tool;
   the recesses are distributed around a screw head axis, extend axially in a direction of the screw head axis, and open into the proximal end face of a free end of the screw head; and
   the recesses are each formed by lateral surfaces that extend from an outer lateral surface enveloping the external thread of the screw head in the direction of the screw head axis and merge into one another in a surface section close to the axis.

5. The bone transplant according to claim 4, further comprising:
   four recesses distributed symmetrically around the screw head axis.

* * * * *